United States Patent [19]
DiNino

[11] Patent Number: 5,535,744
[45] Date of Patent: Jul. 16, 1996

[54] METHOD AND APPARATUS FOR BLOOD CHEMISTRY ANALYSIS

[76] Inventor: Patricia C. DiNino, 68 Robin Ct., Middletown, Conn. 06457

[21] Appl. No.: 333,640

[22] Filed: Nov. 3, 1994

[51] Int. Cl.$^6$ ....................................................... A61B 5/00
[52] U.S. Cl. ............................................................. 128/635
[58] Field of Search ..................................... 128/632, 635, 128/637, 734; 204/400, 412, 416

[56] References Cited

U.S. PATENT DOCUMENTS

| | | | |
|---|---|---|---|
| 4,185,620 | 1/1980 | Hagihara | 128/635 |
| 4,195,641 | 4/1980 | Joines et al. | 128/632 |
| 5,425,868 | 6/1995 | Pedersen | 128/637 |

*Primary Examiner*—Max Hindenburg
*Attorney, Agent, or Firm*—Chilton, Alix & Van Kirk

[57] ABSTRACT

A blood chemistry analyzer for determining the concentration of various chemical compounds or analytes in a patient's blood in a non-invasive manner employs a plurality of electrodes, an isotonic bath, a spectrophotometer, and a control unit. Adhesive electrodes are attached to the patient's skin such that the patient's entire peripheral blood supply system is analyzed. The controller provides a signal to the electrodes that causes the electrodes to develop an electrical charge, or potential, having a magnitude proportional to the detected charge for the analyte of interest. This potential is transmitted to an isotonic bath where it causes a portion of the dissolved salts to separate into anions and cations. The amount of separation is proportional to the magnitude of the electrical potential. Predetermined volumes of the anion/cation saturated isotonic solution are piped into reagent wells containing a reagent corresponding to the specific blood analyte of interest. The test solution is transported to a spectrophotometer where it is analyzed by known methods. The spectrophotometer transmits digitized test data to a microprocessor located in the control unit. The microprocessor performs calculations on these digital values according to algorithms stored in the microprocessor storage unit.

14 Claims, 5 Drawing Sheets

METHOD AND APPARATUS FOR BLOOD CHEMISTRY ANALYSIS

BACKGROUND OF THE INVENTION

This invention relates generally to chemistry analyzers. More particularly, the present invention relates to blood chemistry analyzers.

Current methods and apparatus for blood chemistry analysis require that a blood sample be drawn from the patient. Most patients find it discomforting to provide such blood samples. The pain caused by drawing samples for current methods of blood chemistry analysis is considered a necessary evil that must be endured so that the greater health of the patient may be properly assessed.

Some patients abhor providing blood samples and avoid medical treatment where blood samples are required. Consequently, such patients may not receive needed medical treatment or receive improper treatment.

Blood samples may expose laboratory technicians to harmful pathogens, such as HIV. Although proper procedures reduce the risk of such exposure, procedures cannot account for all eventualities and some risk will remain.

Current methods and apparatus for blood chemistry analysis are generally not portable and are therefore not well suited for use outside of a medical care facility. Consequently, the analysis of blood samples drawn from accident victims and others requiring emergency care must wait until the blood sample, and the patient, arrive at a medical care facility.

SUMMARY OF THE INVENTION

Briefly stated, the invention in a preferred form is a blood chemistry analyzer comprising of a plurality of electrodes, an isotonic bath, a spectrophotometer, and a control unit. The analyzer provides a non-invasive method of determining the concentration of various chemical compounds or analytes in the patient's blood.

Each molecule of a selected analyte has known quantities of protons, neutrons and electrons in its molecular composition. This atomic structure produces a signature or characteristic electrical charge due to the relative positioning of the nuclei of the constituent atoms and the sharing of electrons in the outer electron shells. Electrodes, such as those used in electrocardiograms, are capable of detecting these electrical signatures in a patients peripheral blood supply system. The analyzer detects the characteristic electrical charge of each analyte and measures the total number of such charges that are present in a unit volume of blood, thereby determining the concentration of such analyte in the blood.

Six adhesive electrodes are attached to the patient's skin at various sites on the body. Such placement provides for analysis of the patient's entire peripheral blood supply system. The volume of blood present in a particular patient's peripheral blood supply system is computed by the control unit utilizing easily determined personal data, for example weight, height and sex.

The electrodes develop an electrical charge, or potential, having a magnitude proportional to the detected charge for the analytes present in the patient's blood. This potential is transmitted to the isotonic bath interface circuit board. The control unit provides a signal to the isotonic bath interface board that identifies the specific analyte of interest. The isotonic bath interface board filters the input electrode signal, removing any portion of the input electrode signal that is not attributable to the specific analyte of interest. That portion of the input electrode signal that is attributable to the specific analyte of interest is transmitted to the isotonic bath. This electrical potential is applied to the isotonic bath via an anode and a cathode. The electrical potential causes a portion of the dissolved salts to separate into anions and cations. The amount of separation is proportional to the magnitude of the electrical potential across the anode and cathode.

Predetermined volumes of the anion/cation saturated isotonic solution are piped into a plurality of reagent wells. A reagent corresponding to a specific blood analyte is added to each reagent well and mixed with the isotonic solution to form a test solution. Each test solution is transported to an individual cuvette located in a spectrophotometer. The spectrophotometer has a microflow cell assembly comprising a shuttle holding a plurality cuvettes. The shuttle is driven by a belt along horizontal rails by a stepper motor such that each cuvette can be positioned into the optical path of the spectrophotometer. Each test solution is analyzed by known methods in the spectrophotometer.

The spectrophotometer transmits digitized test data to a microprocessor located in the control unit. The microprocessor performs calculations on these digital values according to one of seven algorithms. The control unit also controls the operation of the spectrophotometer including the gain of the pre-amp, the selection of the filter, movement of the shuttle, incubation, read time and source lamp intensity. The control unit also controls a pump and solenoid operated valves for selecting and aspirating the proper reagent into the reagent well.

An object of the invention is to provide a new and improved method and apparatus for analyzing blood chemistry.

Another object of the invention is to provide a new and improved method and apparatus for analyzing blood chemistry that does not require drawing a blood sample.

A further object of the invention is to provide a new and improved method and apparatus for analyzing blood chemistry that is compact and easily transportable.

Other objects and advantages of the invention will become apparent from the drawings and specification.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

Figure 1:
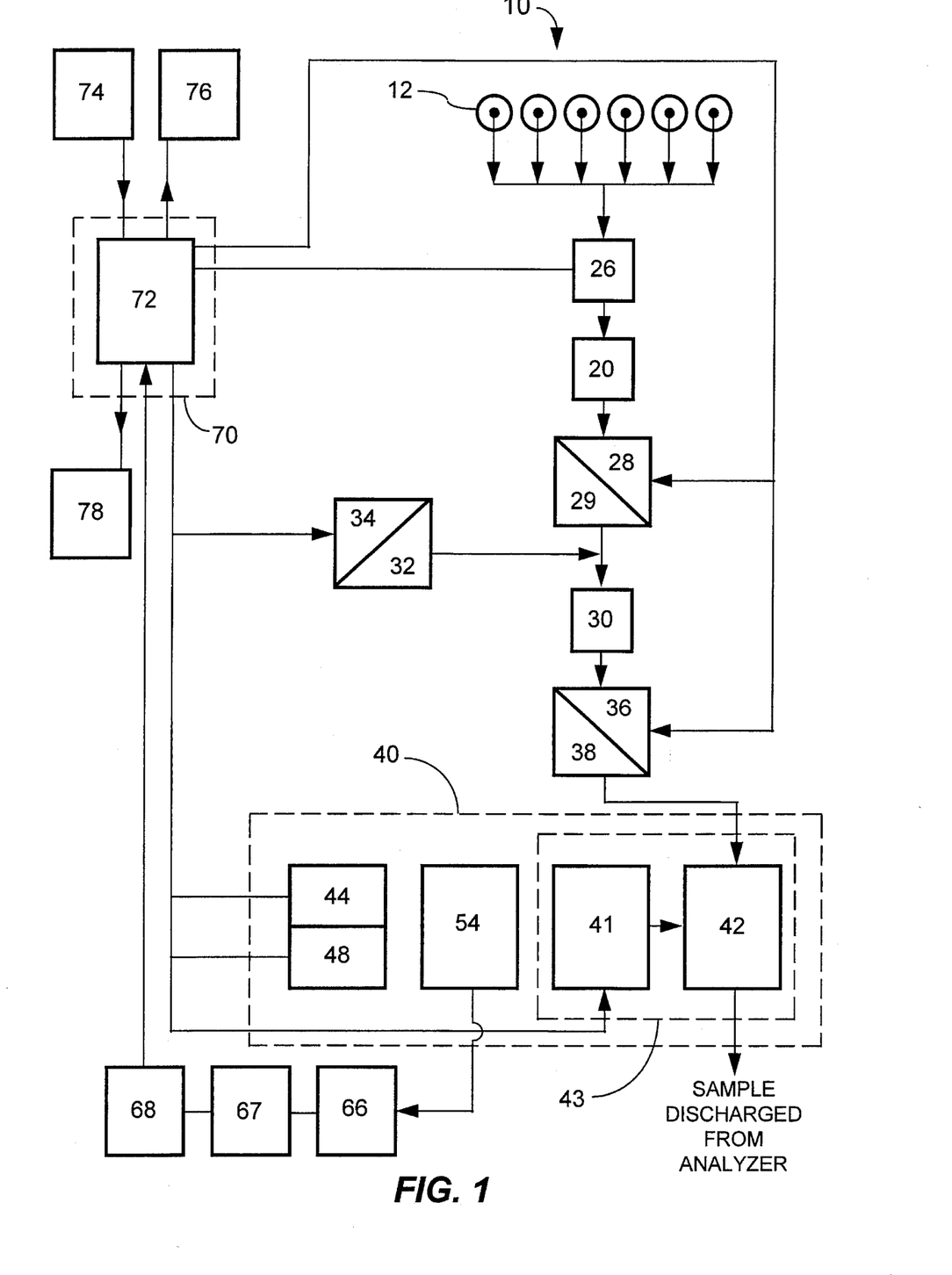
FIG. 1 is a schematic diagram of a blood chemistry analyzer in accordance with the present invention.

With reference to the drawings wherein like numerals represent like parts throughout the several figures, a blood chemistry analyzer in accordance with the present invention is generally designated by the numeral 10. A disclosure document, No. 350530, was filed with the United States Patent and Trademark Office and recorded on Mar. 21, 1994. The analyzer is comprised of a plurality of electrodes 12, an isotonic bath 20, a spectrophotometer 40, and a control unit 70, as shown in FIG. 1. The analyzer 10 provides a non-invasive method of determining the concentration of various chemical compounds, analytes, in the patient's blood. The analyzer 10 detects the characteristic electrical charge of each analyte and measures the total number of such charges that are present in a unit volume of blood, thereby determining the concentration of such analyte in the blood.

Each molecule of a selected analyte has known quantities of protons, neutrons and electrons in its molecular composition. This atomic structure produces a signature or characteristic electrical charge due to the relative positioning of the nuclei of the constituent atoms and the sharing of electrons in the outer electron shells. Characteristics of the various blood analytes are provided in Table 1. Electrodes, such as those used in electrocardiograms, are capable of detecting these electrical signatures in a patients peripheral blood supply system.

supply volume. The electrodes 12 develop an electrical charge, or potential, having a magnitude proportional to the total number of detected fields for the analytes present within the blood. This signal is transmitted to an isotonic bath 20 via electrical leads 14.

Figure 2:
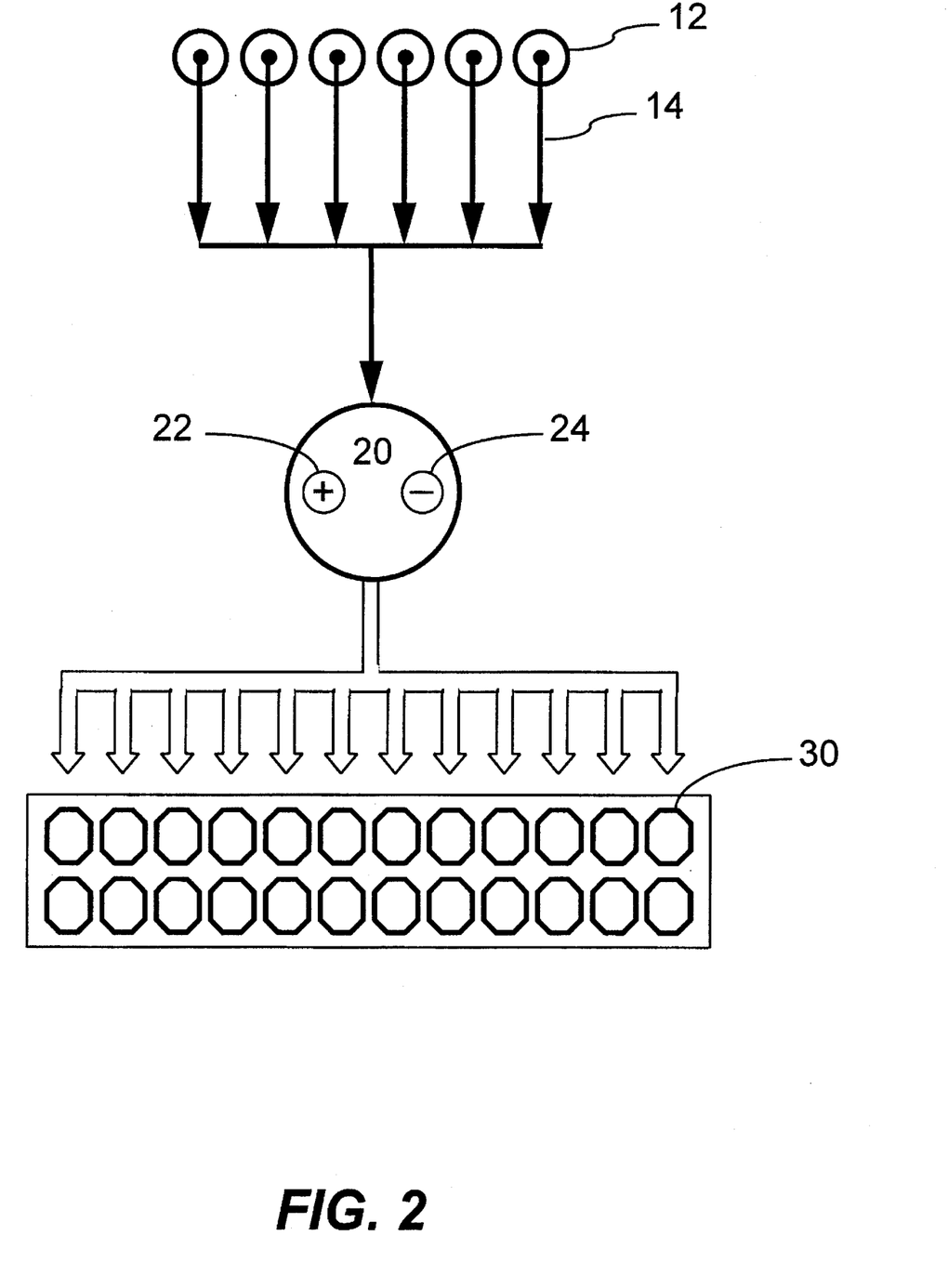
FIG. 2 is a schematic diagram of the electrodes, isotonic bath, and reagent wells of the blood chemistry analyzer of FIG. 1.

The interface board 26 of the isotonic bath 20 receives the potential transmitted from the electrodes 12 and a signal from the controller 70. The interface board 26 is a ENI-401374-16 or equivalent circuit board. The controller signal identifies the specific analyte of interest. The isotonic bath interface board 26 utilizes the controller signal to filter the electrode signal and transmits that portion of the electrode signal attributable to the analyte of interest to the isotonic bath 20. The electrical potential is applied to the solution in the isotonic bath 20 via an anode 22 and a cathode 24 (FIG. 2). The isotonic bath 20 contains a solution of sodium chloride, sodium phosphate, and sodium sulphate anhydrous. The electrical potential causes a portion of the dissolved salts to separate into anions and cations. The amount of separation is proportional to the magnitude of the electrical potential across the anode and cathode.

The control unit 70 controls a pump 28 and solenoid valve 29 to pump predetermined volumes of the anion/cation

TABLE 1

| ANALYTE | WT. (MG/MOLE) | CHARGE | STRUCTURE (ELECTRON SHELLS) |
| --- | --- | --- | --- |
| ALBUMIN | 55.8 ± 1.3 | +2 | 2,18,24,32,23 |
| ALK PHOS | 27.7 ± 2.0 | +1 | 2,18,24,27 |
| ALT | 49.2 ± 1.4 | −3 | 2,18,24,32,19 |
| AMYLASE | 8.8 ± 0.6 | −1 | 2,18,11 |
| AST | 66.9 ± 3.1 | −2 | 2,18,24,32,35 |
| BILI, TOTAL | 74.0 ± 2.4 | +1 | 2,18,24,32,38 |
| CALCIUM | 6.9 ± 0.4 | −2 | 2,1 8,5 |
| CHLORIDE | 91.3 ± 3.0 | −1 | 2,18,24,32,38,15 |
| CHOLESTEROL | 19.1 ± 0.8 | +3 | 2,18,24,9 |
| $CO_2$ | 1.45 ± 0.27 | +2 | 2,1 |
| CPK | 23.0 ± 1.9 | −2 | 2,18,24,17 |
| CREATININE | 3.8 ± 0.5 | +2 | 2,14 |
| GGT | 79.1 ± 1.1 | +1 | 2,18,24,32,38,3 |
| GLUCOSE | 12.7 ± 0.5 | +3 | 2,18,24 |
| HDL | 15.0 ± 0.6 | +3 | 2,18,24,3 |
| IRON | 61.4 ± 1.0 | −2 | 2,18,24,32,29 |
| LDH | 102 ± 2.0 | +2 | 2,18,24,32,38,27 |
| MAGNESIUM | 84.6 ± 2.6 | −3 | 2,18,24,32,38,9 |
| PHOSPHORUS | 97.1 ± 1.7 | +2 | 2,18,24,32,38,20 |
| POTASSIUM | 5.6 ± 0.4 | +1 | 2,18,2 |
| PROTEIN, TOTAL | 44.3 ± 2.9 | +3 | 2,18,24,32,12 |
| SODIUM | 10.8 ± 0.8 | +2 | 2,18,17 |
| TRIGLYCERIDES | 37.2 ± 3.5 | −3 | 2,18,24,32,2 |
| UREA | 32.4 ± 1.9 | −2 | 2,18,24,32 |
| URIC ACID | 2.2 ± 0.3 | −1 | 2,7 |

Figure 5:
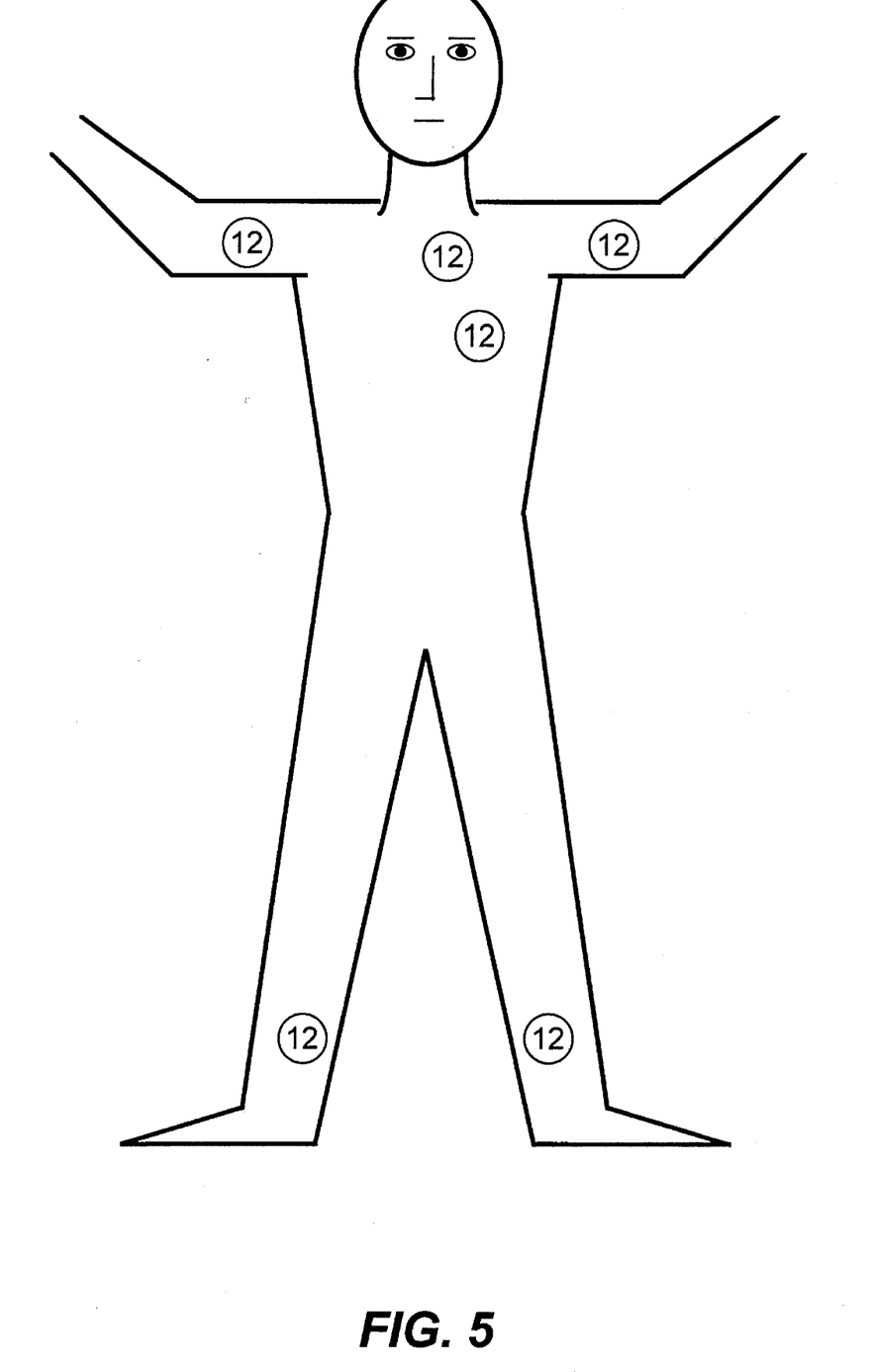
FIGS. 5 is a front perspective view of a patient showing the placement of the electrodes of the blood chemistry analyzer of FIG. 1.

Six adhesive electrodes 12 are applied to the patient's skin at various sites on the body. The electrodes 12 are positioned substantially as shown in FIG. 5. Such placement provides for analysis of the patient's entire peripheral blood supply system. The volume of blood present in a particular patient's peripheral blood supply system can be determined by applying easily determined personal data to readily available statistical models. For example, inputing the patients weight, height and sex into the model will provide a calculated blood volume that is within 3% of patient's actual peripheral blood saturated isotonic solution from the isotonic bath 20 to a plurality of reagent wells 30. A reagent corresponding to a specific blood analyte is added to each reagent well 30 and mixed with the isotonic solution to form a test solution. Table 2 lists the blood analytes and the corresponding reagent. Each test solution is transported to an individual cuvette 42 located in a spectrophotometer 40.

TABLE 2

| ANALYTE TEST | CORRESPONDING REAGENTS |
| --- | --- |
| Albumin | bromcresol green |

TABLE 2-continued

| ANALYTE TEST | CORRESPONDING REAGENTS |
|---|---|
| Alkaline Phosphatase | p-nitrophenyl phosphate |
| ALT (alanine amino transferase) | L-alanine, oxoglutarate |
| Amylase | ethylidene, nitrophenyl, D-maltohrptaside |
| AST (aspartate amino transferase) | L-aspartate, oxoglutarate |
| Bilirubin, Total | sulfanilic acid, sodium nitrite |
| Calcium | arsenazo III |
| Carbon Dioxide | phosphoenol pyruvate |
| Cholesterol | cholesterol oxidase and esterase, peroxidase |
| Chloride | deionized water |
| Creatine Kinase | creatine phosphate, adenosine diphosphate |
| Creatinine | picric acid, sodium hydroxide |
| Glucose | adenosine triphosphate, hexokinase glucose-6-phosphate dehydrogenase |
| GGT (y-glutamyl transferase) | L-y-glutamyl-3-carboxy-4-nitroanilide |
| HDL (high density lipoprotein) | phosphotungstic acid, magnesium chloride |
| Iron | ferrozine, hydroxylamine hydrochloride |
| LDH (lactate dehydrogenase) | lithium lactate, hydroxymethyl-aminomethane |
| Magnesium | magon sulfonate |
| Phosphorus, inorganic | ammonium molybate, sulfuric acid |
| Potassium | deionized water |
| Protein, Total | sodium hydroxide, copper sulfate |
| Sodium | deionized water |
| Triglycerides | glycerol kinase, glycerol phosphate, oxidase, peroxidase |
| Urea | urease, oxoglutarate |
| Uric Acid | uricase, peroxidase, aminoantipyrine |

Figure 3:
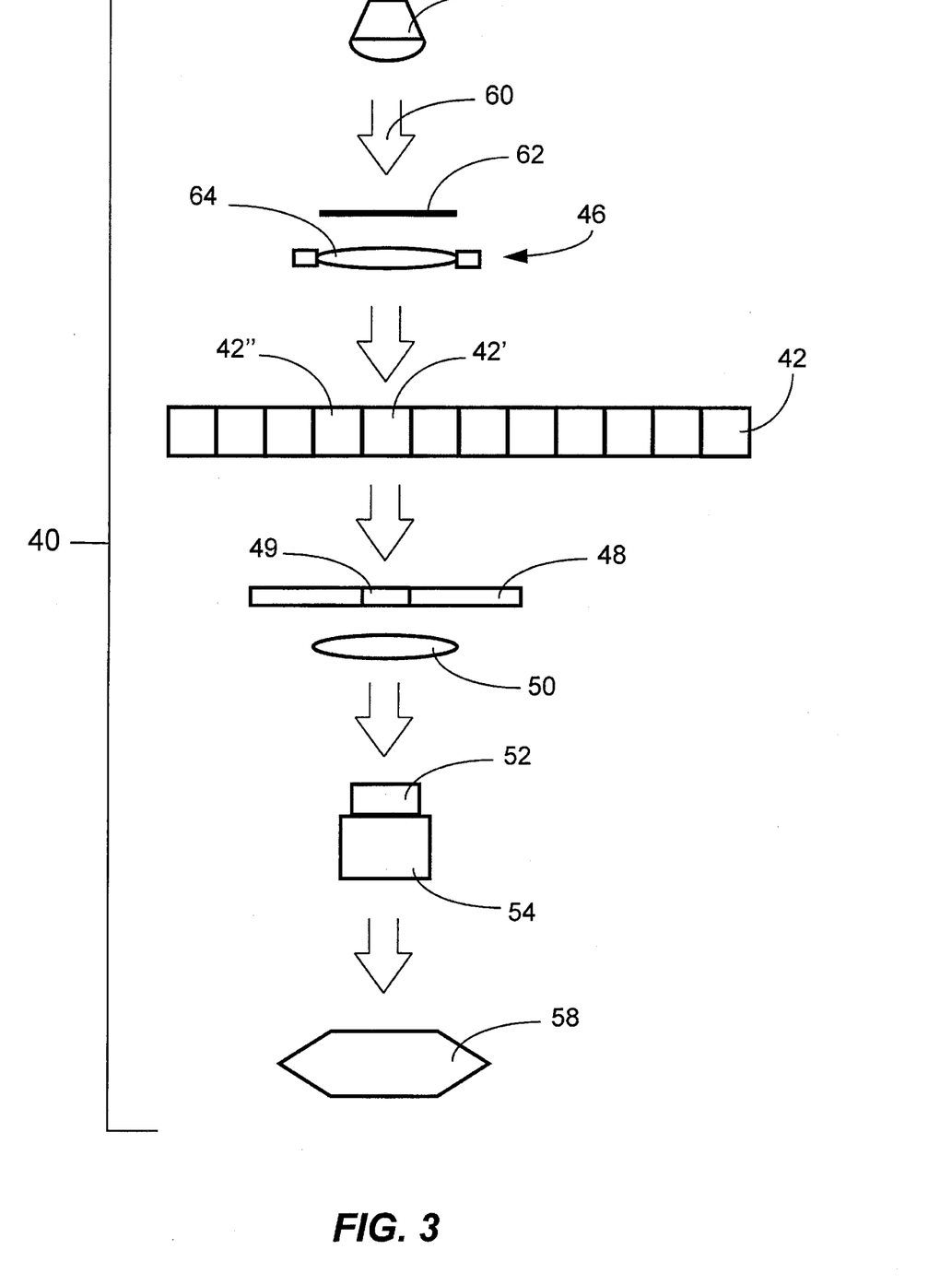
FIG. 3 is a schematic diagram of the spectrophotometer of the blood chemistry analyzer of FIG. 1.

The spectrophotometer 40 has a microflow cell assembly 43 comprising a shuttle 41 holding a maximum of twenty four (24) cuvettes 42. The shuttle 41 is driven by a belt along horizontal rails by a stepper motor (not shown) such that each cuvette 42 can be positioned into the optical path 60 of the spectrophotometer 40.

The spectrophotometer 40 comprises a source lamp assembly 44, a collimator lens assembly 46, filter wheel 48, collector lens 50, photodiode 52, pre-amp 54, and refractometer 58. The filter wheel 48 has nine filters 49 providing the following filter settings: 340, 380, 405, 450, 500, 546, 575, 600, and 650 nanometers. A filter 49 is selected by the control unit 70 to provide the desired wavelength of monochromatic light.

The spectrophotometer 40 is first calibrated using blank, reference and control readings. Each cuvette 42' is shuttled into the optical path 60. The spectrophotometer 40 measures the optical absorbance of the test solution, the measurement is recorded, and the next cuvette 42" is shuttled into the optical path 60. The reading interval for each cuvette 42 is approximately 200 milliseconds. During this interval, multiple readings are obtained and averaged to yield one statistical data point.

The microflow cell assembly 43 has a 33 microliter internal volume and 600 microliter reading volume. The spectrophotometer has photometric linearity of greater than 1%, with photometric accuracy of plus or minus 1%.

The optical path 60 begins at the source lamp assembly 44. A broad spectrum of light, consisting of many different wavelengths, is generated by a tungsten halogen bulb (not shown) in the source lamp assembly 44. Incandescent light is gathered in the collimator lens assembly 46, where it is passed through a light barrier 62 having a rectangular aperture and focused into a parallel beam as it exits through the collimator lens 64. The light beam then passes through the transparent cuvettes 42 held in the shuttle 41. Each cuvette 42 represents 1 cm of fluid path length. The beam is then sent through a selected band pass filter 49 located on the filter wheel 48. The selected filter 49 only allows a narrow wavelength band to pass through, since different colorimetric reactions show more measurable light absorbance changes at specific wavelengths. After passing through the filter 49, the light beam is gathered at the collector lens 50, where it is focused and introduced into the light-sensitive silicon photodiode 52 of the pre-amp 54. The pre-amp 54 is an electrical amplifier with computer programmable gain factors. The output of the photodiode 52 and pre-amp 54 is a voltage which varies directly with the light passing through the cuvette 42 and filter 49.

The signal is now passed to an analog processor 66 with dark level restoration and calibration functions. A subsequent log amp 67 is used to convert the transmittance signal to a voltage which is an analog of optical absorbance. This voltage is then converted to a digital value by a 12 bit A/D converter 68.

Figure 4:
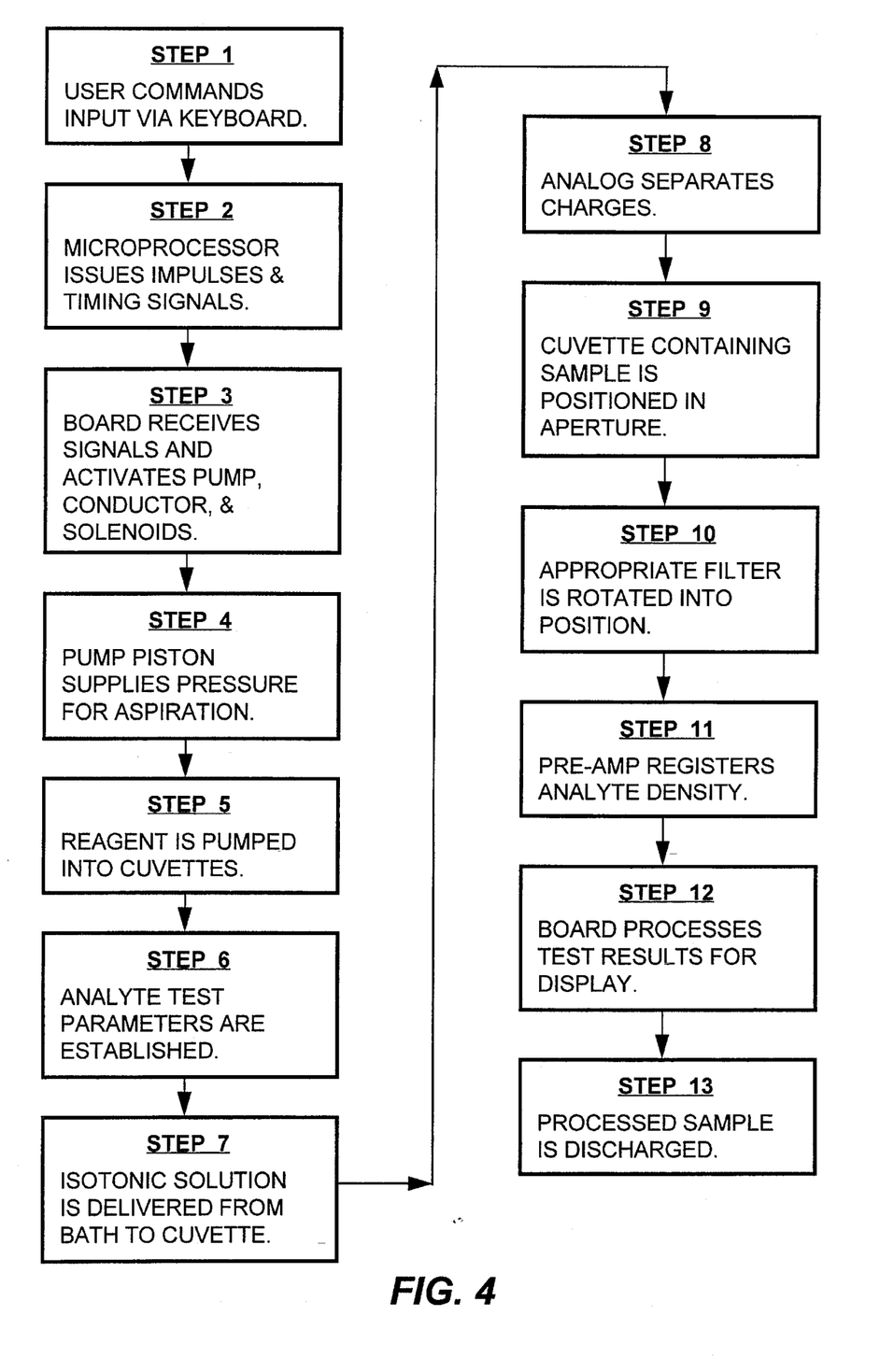
FIG. 4 is a schematic diagram of the mode of operation of the control unit of the blood chemistry analyzer of FIG. 1.

A microprocessor 72, preferably located in the control unit 70, performs calculations on these digital values according to one of seven algorithms. The control unit controls the gain of the pre-amp 54, the selection of the filter 49, movement of the shuttle 41, incubation, and read time. Source lamp 44 intensity is controlled by the control unit 70 via an 8 bit D/A converter and a lamp power control circuit (not shown). The control unit 70 controls a pump 36 and solenoid operated valve 38 for transporting the test solution from the reagent wells 30 to the cuvettes 42. The control unit 70 also controls a pump 32 and solenoid operated valves 34 for selecting and aspirating the proper reagent into the reagent well 30.

For temperature sensitive tests, temperature is controlled by a ribbon heater, calibrated thermistor, and temperature control circuit (not shown).

In a preferred embodiment, the analyzer's 10 electronics include three micro P280's, a 32 KB EPROM, and a 32 KB non-volatile RAM. Self diagnostics are monitored automatically with an external interface.

The control unit 70 controls the operation of the analyzer 10, as shown in FIG. 1. Technician interface is accomplished through the keyboard 74, display 76, and printer 78. The keyboard 74 is a membrane switch configuration, consisting of a numerical keypad and function keys for entry of chemistry parameters and run instructions. The technician first loads cuvettes 42 containing the proper reagents into the shuttle 41. The technician then enters patient data such as identification, sex, age and weight. This data is utilized to calculate the total volume of the peripheral blood supply. The technician then enters preprogrammed profiles of tests or individual tests to be run by touching the "profile" key followed by profile number or by touching the "chemistry" key followed by individual test number and finally touching the "continue" key. Next, the technician attaches the electrodes to the patient at the positions indicated in FIG. 5 and touches the "run" key.

Upon receipt of the chemistry parameters and run instructions, the microprocessor 72 issues control signals to pumps 28 and 32 and solenoid valves 29 and 34 to deliver solution from the isotonic bath 20 and reagents to the reagent well 30. The microprocessor 72 then issues control signals to pump 36 and solenoid valve 38 to transport the test solution to the cuvettes 42. The microprocessor 72 establishes the test parameters and rotates the filter wheel 48 to select the proper filter 49. The microprocessor 72 receives the digital signal from A/D converter 68 and calculates the concentration of the selected analyte. An 8-digit LED display 76 is used to display user entry verifications, as well as test results.

The analyzer 10 may also be equipped to interface with conventional PC hardware (i.e. 486-type processor, monitor, and laser printer) for enhanced monitoring and printing capabilities.

Operation of the analyzer 10 has been proven in laboratory experiments. The peripheral blood chemistry of a number of test subjects was analyzed utilizing the analyzer 10. A blood sample was also withdrawn from each subject and analyzed by conventional methods using a Biochem Laboratory Systems ATAC 6000™ blood chemistry analyzer. In ten trials both analysis were conducted on the same day with the analysis utilizing the analyzer 10 being performed prior to the analysis by conventional means. The results of the trials are provided in Table 3 below.

Table 4 provides the average, maximum and minimum variation between the measured values for each of the electrolytes.

While preferred embodiments have been shown and described, various modifications and substitutions may be made thereto without departing from the spirit and scope of the invention. Accordingly, it is to be understood that the present invention has been described by way of illustration and not limitation.

TABLE 3

| Electrolyte | Test 1 Analyzer | Test 1 Conventional | Test 2 Analyzer | Test 2 Conventional | Test 3 Analyzer | Test 3 Conventional | Test 4 Analyzer | Test 4 Conventional |
|---|---|---|---|---|---|---|---|---|
| Albumin | 4.0 | 4.2 | 3.7 | 3.9 | 4.1 | 4.0 | 4.4 | 4.3 |
| Akaline Phosphatase | 59. | 63. | 75. | 72. | 68. | 71. | 62. | 56. |
| Amylase | 45. | 42. | 66. | 70. | 59. | 56. | 42. | 47. |
| Bilirubin, Total | 0.7 | 0.8 | 1.0 | 0.9 | 1.0 | 0.9 | 0.9 | 0.8 |
| Bun | 11. | 11. | 13. | 13. | 10. | 11. | 7. | 9. |
| Calcium | 9.4 | 9.7 | 9.7 | 9.4 | 9.8 | 9.8 | 9.9 | 9.6 |
| Carbon Dioxide | 22.1 | 22.7 | 22.4 | 23.0 | 22.7 | 23.3 | 22.2 | 22.9 |
| Chloride | 108. | 106. | 107. | 105. | 107. | 106. | 107. | 107. |
| Cholesterol, Total | 272 | 264 | 275. | 268. | 260. | 259. | 258. | 251. |
| Cholesterol, HDL | 96. | 92. | 99. | 94. | 91. | 91. | 101. | 98. |
| CPK | 74. | 70. | 63. | 65. | 91. | 99. | 86. | 81. |
| Creatinine | 0.6 | 0.8 | 1.0 | 0.8 | 99. | 1.0 | 0.9 | 0.8 |
| GGT | 13. | 15. | 15. | 17. | 11. | 9. | 12. | 12. |
| Glucose | 83. | 79. | 73. | 68. | 92. | 86. | 80. | 74. |
| GOT | 13. | 14. | 16. | 13. | 10. | 11. | 9. | 10. |
| GPT | 12. | 15. | 16. | 11. | 12. | 12. | 14. | 17. |
| Iron, Total | 89. | 83. | 94. | 89. | 99. | 107. | 92. | 90. |
| LDH | 124. | 118. | 119. | 124. | 126. | 131. | 117. | 114. |
| Magnesium | 2.1 | 2.0 | 2.0 | 1.8 | 2.1 | 2.0 | 1.9 | 1.9 |
| Phosphorus | 3.7 | 3.9 | 3.8 | 4.1 | 3.9 | 3.7 | 3.6 | 3.8 |
| Potassium | 4.3 | 4.1 | 3.5 | 3.8 | 3.6 | 3.8 | 4.4 | 4.1 |
| Sodium | 145. | 143. | 140. | 143. | 143. | 140. | 145. | 142. |
| Total Protein | 7.0 | 7.4 | 7.9 | 7.5 | 7.4 | 7.7 | 7.6 | 7.9 |
| Triglycerides | 79. | 75. | 106. | 106. | 99. | 94. | 81. | 85. |
| Uric Acid | 34 | 3.6 | 3.5 | 3.9 | 3.5 | 3.4 | 3.4 | 3.7 |

| Electrolyte | Test 5 Analyzer | Test 5 Conventional | Test 6 Analyzer | Test 6 Conventional | Test 7 Analyzer | Test 7 Conventional | Test 8 Analyzer | Test 8 Conventional |
|---|---|---|---|---|---|---|---|---|
| Albumin | 3.7 | 3.9 | 4.0 | 4.3 | 3.9 | 4.1 | 3.9 | 3.9 |
| Alkaline Phosphatase | 66. | 62. | 62. | 56. | 69. | 62. | 79. | 74. |
| Amylase | 57. | 52. | 48. | 48. | 65. | 59. | 71. | 67. |
| Bilirubin, Total | 0.9 | 0.9 | 0.8 | 0.8 | 0.9 | 1.0 | 0.9 | 1.0 |
| Bun | 15. | 16. | 12. | 14. | 10. | 11. | 12. | 13. |
| Calcium | 10.0 | 9.7 | 9.6 | 9.9 | 9.5 | 9.7 | 9.6 | 9.4 |
| Carbon Dioxide | 22.7 | 23.4 | 22.1 | 22.9 | 22.7 | 23.4 | 22.2 | 23.0 |
| Chloride | 105. | 106. | 107. | 105. | 104. | 106. | 107. | 106. |
| Cholesterol, Total | 249. | 246. | 244. | 240. | 239. | 236. | 245. | 239. |
| Cholesterol, HDL | 98. | 108. | 95. | 106. | 92. | 100. | 90. | 98. |

TABLE 3-continued

| | | | | | | | | |
|---|---|---|---|---|---|---|---|---|
| CPK | 71. | 65. | 83. | 77. | 70. | 64. | 81. | 75. |
| Creatinine | 1.0 | 0.8 | 0.9 | 0.7 | 1.0 | 0.9 | 1.0 | 0.8 |
| GGT | 14. | 12. | 14. | 14. | 12. | 12. | 13. | 14. |
| Glucose | 85. | 81. | 102. | 94. | 79. | 86. | 107. | 102. |
| GOT | 11. | 11. | 10. | 12. | 10. | 9. | 11. | 12. |
| GPT | 14. | 14. | 12. | 14. | 15. | 13. | 15. | 15. |
| Iron, Total | 101. | 94. | 89. | 93. | 92. | 101. | 94. | 97. |
| LDH | 123. | 119. | 128. | 122. | 121. | 119. | 124. | 120. |
| Magnesium | 2.0 | 1.8 | 1.9 | 2.0 | 1.9 | 1.9 | 1.9 | 2.1 |
| Phosphorus | 3.9 | 3.6 | 3.5 | 3.6 | 3.7 | 3.9 | 3.6 | 3.5 |
| Potassium | 4.5 | 4.3 | 4.3 | 4.1 | 4.1 | 3.9 | 4.0 | 4.2 |
| Sodium | 145. | 145. | 140. | 141. | 144. | 143. | 135. | 138. |
| Total Protein | 7.1 | 7.6 | 7.4 | 7.1 | 7.6 | 7.8 | 7.1 | 6.9 |
| Triglycerides | 73. | 68. | 89. | 95. | 79. | 87. | 120. | 113. |
| Uric Acid | 3.4 | 3.2 | 3.5 | 3.5 | 3.5 | 3.4 | 3.4 | 3.2 |

| | Test 9 | | Test 10 | |
|---|---|---|---|---|
| Electrolyte | Analyzer | Conventional | Analyzer | Conventional |
| Albumin | 4.1 | 4.3 | 3.8 | 4.0 |
| Alkaline Phosphatase | 70. | 68. | 67. | 73. |
| Amylase | 80. | 74. | 73. | 66. |
| Bilirubin, Total | 0.9 | 0.8 | 0.9 | 0.8 |
| Bun | 14. | 15. | 13. | 13. |
| Calcium | 9.8 | 9.6 | 9.1 | 9.4 |
| Carbon Dioxide | 22.6 | 23.5 | 22.0 | 22.9 |
| Chloride | 105. | 105. | 106. | 106. |
| Cholesterol, Total | 248. | 242. | 249. | 240. |
| Cholesterol, HDL | 88. | 93. | 94. | 96. |
| CPK | 85. | 79. | 79. | 71. |
| Creatinine | 0.9 | 0.9 | 0.9 | 1.0 |
| GGT | 9. | 12. | 10. | 10. |
| Glucose | 82. | 77. | 98. | 93. |
| GOT | 12. | 10. | 12. | 10. |
| GPT | 12. | 12. | 14. | 13. |
| Iron, Total | 88. | 90. | 82. | 88. |
| LDH | 120. | 117. | 126. | 121. |
| Magnesium | 2.0 | 1.9 | 1.9 | 2.0 |
| Phosphorus | 3.6 | 3.7 | 3.9 | 3.8 |
| Potassium | 4.2 | 3.9 | 4.2 | 4.0 |
| Sodium | 143. | 140. | 142. | 143. |
| Total Protein | 7.5 | 7.1 | 7.4 | 7.4 |
| Triglycerides | 89. | 83. | 65. | 69. |
| Uric Acid | 3.5 | 3.3 | 3.6 | 3.5 |

TABLE 4

| Electrolyte | Avg. variation | Max. variation | Min. variation |
|---|---|---|---|
| Albumin | 2.8 | 4.8 | 0.0 |
| Alkaline Phosphate | 4.7 | 7.3 | 1.9 |
| Amylase | 4.8 | 7.4 | 0.0 |
| Bilirubin, Total | 6.1 | 8.7 | 0.0 |
| Bun | 5.3 | 16.0 | 0.0 |
| Calcium | 1.7 | 2.2 | 0.0 |
| Carbon Dioxide | 2.1 | 2.7 | 1.7 |
| Chloride | 0.7 | 1.3 | 0.0 |
| Cholesterol, Total | 1.4 | 2.5 | 0.3 |
| Cholesterol, HDL | 3.8 | 7.2 | 0.0 |
| CPK | 5.0 | 7.2 | 2.1 |
| Creatinine | 11.1 | 18.2 | 0.0 |
| GGT | 6.5 | 18.2 | 0.0 |
| Glucose | 4.3 | 5.6 | 3.2 |
| GOT | 8.2 | 14.3 | 0.0 |
| GPT | 7.8 | 26.3 | 0.0 |
| Iron, Total | 3.7 | 6.1 | 1.5 |
| LDH | 2.4 | 3.3 | 1.1 |
| Magnesium | 3.8 | 7.1 | 0.0 |
| Phosphorus | 3.2 | 5.4 | 1.7 |
| Potassium | 3.8 | 5.4 | 3.1 |
| Sodium | 0.9 | 1.5 | 0.0 |
| Total Protein | 2.7 | 4.5 | 0.0 |
| Triglycerides | 3.8 | 6.3 | 0.0 |

TABLE 4-continued

| Electrolyte | Avg. variation | Max. variation | Min. variation |
|---|---|---|---|
| Uric Acid | 3.4 | 7.1 | 0.0 |

What is claimed is:

1. A method of analyzing a patients blood, the blood having a plurality of analytes, each of the analytes having a characteristic electrical charge and being composed of a plurality of identical molecules, each molecule carrying a unit of the charge, the concentration of the analyte being defined by the number of molecules present within a unit volume of the blood, the method comprising the steps of:

(a) attaching a plurality of electrodes to the patient;

(b) detecting the characteristic charge of an analyte present in the patient's blood;

(c) transmitting an electrical signal proportional to the characteristic charge to an isotonic bath wherein said signal causes the anions and cations present in the bath to separate thereby creating a reactive solution, wherein the amount of separation is proportional to the magnitude of the signal;

(d) mixing a reagent with the reactive solution to form a test solution;

(e) analyzing the test solution; and (f) displaying the analysis results.

2. The method of claim 1 wherein step (e) comprises the steps of:

(1) measuring the concentration of the test solution with a spectrophotometer;

(2) storing the measured value;

(3) digitizing the measured value with an A/D converter;

(4) transmitting the digitized value to a microprocessor; and (5) calculating the amount of analyte by applying the digitized value to a plurality of algorithms.

3. The method of claim 2 wherein steps (1) through (5) are repeated wherein multiple readings are obtained.

4. The method of claim 3 wherein step (2) includes the step of averaging the multiple readings.

5. The method of claim 1 wherein said reagent is selected from the group comprising bromcresol green; p-nitrophenyl phosphate; L-alanine, oxoglutarate; sulfanilic acid, sodium nitrite; arsenazo III; phosphoenol pyruvate; cholesterol oxidase and esterase, peroxidase; deionized water; creatine phosphate, adenosine diphosphate; picric acid, sodium hydroxide; adenosine triphosphate, hexokinase glucose-6-phosphate dehydrogenase;L-y-glutamyl-3-carboxy-4-nitroanilide;phosphotungstic acid, magnesium chloride; ferrozine, hydroxylamine hydrochloride; lithium lactate, hydroxymethyl-aminomethane; magon sulfonate; ammonium molybate, sulfuric acid; sodium hydroxide, copper sulfate; glycerol kinase, glycerol phosphate, oxidase, peroxidase; urease, oxoglutarate; and uricase, peroxidase, aminoantipyrine.

6. A chemistry analyzer for analyzing a patient's blood, the blood having a plurality of analytes, each of the analytes having a characteristic electrical charge and being composed of a plurality of identical molecules, each molecule carrying a unit of the charge, the concentration of the analyte being defined by the number of molecules present within a unit volume of the blood, the analyzer comprising:

detector means, said detector means comprising a plurality of electrodes, each of said electrodes being mountable on the patient and comprising means for detecting units of at least one characteristic electrical charge and transmitting a signal having a magnitude proportional to the number units of charge detected;

isotonic bath means comprising a pair of electrodes defining an anode and a cathode and a first solution composed of water and at least one salt, said electrodes being in electrical communication with said detector means for receiving said signal wherein said signal applies an electrical potential to said electrodes, the electrical potential having a magnitude proportional to said magnitude of said signal, whereby said electrical potential causes said salt to separate into a number of anions and cations thereby defining a second solution, said number of cations and anions being proportional to said magnitude of said electrical potential;

means for analyzing a portion of said second solution wherein said analyzer means determines the concentration of the analyte within the patient's blood.

7. The chemistry analyzer of claim 6 wherein said analyzer means comprises a spectrophotometer.

8. The chemistry analyzer of claim 7 wherein said analyzer means further comprises container means for receiving a reagent and a portion of said second solution, said reagent and said portion defining a third solution, said spectrophotometer comprising measurement means for measuring the optical absorbance of said third solution and signal means for providing a signal proportional to said optical absorbance.

9. The chemistry analyzer of claim 8 further comprising logic means and memory means coupled to said logic means wherein said memory means contains a plurality of analysis programs, said optical absorbance signal being received by said logic means, said logic means applying a said analysis program to said signal whereby said logic means determines the concentration of the detected analyte.

10. The chemistry analyzer of claim 9 further comprising display means.

11. The chemistry analyzer of claim 8 wherein said reagent is selected from the group comprising bromcresol green; p-nitrophenyl phosphate; L-alanine, oxoglutarate; sulfanilic acid, sodium nitrite; arsenazo III; phosphoenol pyruvate; cholesterol oxidase and esterase, peroxidase; deionized water; creatine phosphate, adenosine diphosphate; picric acid, sodium hydroxide; adenosine triphosphate, hexokinase glucose-6-phosphate dehydrogenase; L-y-glutamyl-3- carboxy-4-nitroanilide; phosphotungstic acid, magnesium chloride; ferrozine, hydroxylamine hydrochloride; lithium lactate, hydroxymethylaminomethane; magon sulfonate; ammonium molybate, sulfuric acid; sodium hydroxide, copper sulfate; glycerol kinase, glycerol phosphate, oxidase, peroxidase; urease, oxoglutarate; and uricase, peroxidase, aminoantipyrine.

12. A chemistry analyzer for analyzing a patient's blood, the blood having a plurality of analytes, each of the analytes having a characteristic electrical charge and being composed of a plurality of identical molecules, each molecule carrying a unit of the charge, the concentration of the analyte being defined by the number of molecules present within a unit volume of the blood, the analyzer comprising:

detector means, said detector means comprising a plurality of electrodes, each of said electrodes being mountable on the patient and comprising means for detecting units of at least one characteristic electrical charge and transmitting a signal having a magnitude proportional to the number units of charge detected;

isotonic bath means comprising a pair of electrodes defining an anode and a cathode and a first solution composed of water and at least one salt, said electrodes being in electrical communication with said detector means for receiving said signal wherein said signal applies an electrical potential to said electrodes, the electrical potential having a magnitude proportional to said magnitude of said signal, whereby said electrical potential causes said salt to separate into a number of anions and cations thereby defining a second solution, said number of cations and anions being proportional to said magnitude of said electrical potential;

means for analyzing a portion of said second solution wherein said analyzer means determines the concentration of the analyte within the patient's blood, said analyzer means comprising a spectrophotometer having container means for receiving a reagent and a portion of said second solution, said reagent and said portion defining a third solution, said spectrophotometer comprising measurement means for measuring the optical absorbance of said third solution and signal means for providing a signal proportional to said optical absorbance.

13. The chemistry analyzer of claim 12 further comprising logic means, memory means coupled to said logic means and display means wherein said memory means contains a plurality of analysis programs, said optical absorbance signal being received by said logic means, said logic means applying a said analysis program to said signal whereby said logic means determines and displays the concentration of the detected analyte.

14. The chemistry analyzer of claim 13 wherein said reagent is selected from the group comprising bromcresol green; p-nitrophenyl phosphate; L-alanine, oxoglutarate; sulfanilic acid, sodium nitrite; arsenazo III; phosphoenol pyruvate; cholesterol oxidase and esterase, peroxidase; deionized water; creatine phosphate, adenosine diphosphate; picric acid, sodium hydroxide; adenosine triphosphate, hexokinase glucose-6-phosphate dehydrogenase; L-y-glutamyl-3- carboxy-4-nitroanilide; phosphotungstic acid, magnesium chloride; ferrozine, hydroxylamine hydrocthloride; lithium lactate, hydroxymethylaminomethane; magon sulfonate; ammonium molybate, sulfuric acid; sodium hydroxide, copper sulfate; glycerol kinase, glycerol phosphate, oxidase, peroxidase; urease, oxoglutarate; and uricase, peroxidase, aminoantipyrine.

* * * * *